(12) United States Patent
Zahynacz

(10) Patent No.: US 11,751,973 B2
(45) Date of Patent: Sep. 12, 2023

(54) LOCKABLE, HYDRAULIC SURGICAL SUPPORT APPARATUS

(71) Applicant: Smith & Nephew, Inc., Memphis, TN (US)

(72) Inventor: Daniel Zahynacz, Somerville, MA (US)

(73) Assignee: SMITH & NEPHEW, INC., Memphis, TN (US)

( * ) Notice: Subject to any disclaimer, the term of this patent is extended or adjusted under 35 U.S.C. 154(b) by 520 days.

(21) Appl. No.: 16/604,608

(22) PCT Filed: Apr. 13, 2018

(86) PCT No.: PCT/US2018/027627
§ 371 (c)(1),
(2) Date: Oct. 11, 2019

(87) PCT Pub. No.: WO2018/204055
PCT Pub. Date: Nov. 8, 2018

(65) Prior Publication Data
US 2020/0179080 A1 Jun. 11, 2020

Related U.S. Application Data

(60) Provisional application No. 62/500,577, filed on May 3, 2017.

(51) Int. Cl.
*A61B 90/50* (2016.01)
*A61B 46/10* (2016.01)
(Continued)

(52) U.S. Cl.
CPC ............ *A61B 90/50* (2016.02); *A61B 46/10* (2016.02); *A61G 13/12* (2013.01);
(Continued)

(58) Field of Classification Search
CPC .............. A61B 90/50; A61B 46/10; A61B 2017/00539; A61B 2017/00973;
(Continued)

(56) References Cited

U.S. PATENT DOCUMENTS

| 2002/0014567 A1* | 2/2002 | King | F16C 11/106 248/159 |
| 2008/0289636 A1* | 11/2008 | Lacroix | A61G 13/0063 128/845 |
| 2010/0312291 A1* | 12/2010 | Mast | A61B 17/885 606/86 B |

FOREIGN PATENT DOCUMENTS

DE 10234271 A1 * 2/2004 ............ F16M 11/14

OTHER PUBLICATIONS

EP Office Action for Patent Application No. 18722816.8 dated Sep. 16, 2020, 8 pages.

(Continued)

*Primary Examiner* — Brooke Labranche
(74) *Attorney, Agent, or Firm* — Burns & Levinson, LLP; Joseph M. Maraia; Marlo Schepper Grolnic

(57) ABSTRACT

A surgical support apparatus for supporting and positioning a patient's limb or an instrument during surgical procedures. The apparatus consists of an adjustable structural component which houses a separate hydraulic system used for locking and unlocking the structural apparatus. The structural component includes three lockable joints and two rigid support arms. Each joint houses a hydraulic piston and a locking ring. Hydraulic pressure is supplied to the joints by an electric motor and pump and is controlled by an electric circuit, pressure sensors and valves. When hydraulic pressure is applied, the pistons are activated, locking the joints. Hydraulic pressure can also be released to unlock the joints through a user control circuit. The structural component also (Continued)

includes a universal rail clamp to attach the device to a support structure and a distal quick connect for attachment of accessory devices.

18 Claims, 8 Drawing Sheets

(51) Int. Cl.
    *A61G 13/12*     (2006.01)
    *A61B 90/57*     (2016.01)
    *A61B 17/00*     (2006.01)

(52) U.S. Cl.
    CPC ..... *A61G 13/1235* (2013.01); *A61G 13/1245* (2013.01); *A61B 2017/00539* (2013.01); *A61B 2017/00973* (2013.01); *A61B 2090/571* (2016.02)

(58) Field of Classification Search
    CPC ........ A61B 2090/571; A61B 2090/508; A61G 13/12; A61G 13/1235; A61G 13/1245
    See application file for complete search history.

(56) References Cited

OTHER PUBLICATIONS

Chinese Application No. 2018800258804 The First Office Action & Search Report dated Jun. 15, 2022.
Chinese Application No. 2018800258804 The Second Office Action & Search Report.

\* cited by examiner

LOCKABLE, HYDRAULIC SURGICAL SUPPORT APPARATUS

CROSS-REFERENCE TO RELATED APPLICATIONS

This application is the U.S. national phase entry under 35 U.S.C. § 371 of International Application No. PCT/US2018/027627, filed Apr. 13, 2018, entitled LOCKABLE, HYDRAULIC SURGICAL SUPPORT APPARATUS, which in turn claims priority to and benefit of U.S. Provisional Application No. 62/500,577, filed May 3, 2017, the contents of which are incorporated herein by reference in their entirety for all purposes.

FIELD

This disclosure relates to a surgical support apparatus and, more particularly, to an adjustable, lockable, arm-like support capable of holding tools, instruments and the like.

BACKGROUND

In certain surgical procedures, it is often necessary to hold a patient's body or a limb in a specific orientation or series of orientations that are to be fixed and maintained for extended periods, for example, during orthopedic surgery on a shoulder or knee joint. In addition, it may be necessary to manipulate and hold several tools or instruments to effect the surgical procedure. Even a single instrument may have several controls which require manual manipulation, resulting in the need for additional staff or devices to hold the instrument or instruments during the course of a surgical procedure.

Currently, there are a number of surgical support devices known in the art, many of which are mechanical systems utilizing structural arms that are positioned and held by gears, springs, or clutches. Some of these devices use hydraulic pressure for locking and unlocking the joints between the arms of the device in order to rotate and hold the arms in place. However, some hydraulic devices combine both the structural apparatus and the hydraulic pressure system into one component, for example, by using at least one of the support arms as both a structural member and a hydraulic fluid conduit. Combining the two functions into one component restricts the selection of materials available for the structural support and the hydraulic tubing. This in turn may increase the size and weight of the device, limiting its function and desirability.

BRIEF SUMMARY

Described herein is a surgical support apparatus that can be used to support and position a patient's limb or an instrument during surgical procedures. The apparatus consists of an adjustable structural component which houses a separate hydraulic system used for locking and unlocking the structural apparatus. The structural component includes three lockable joints and two rigid support arms. Each joint houses a hydraulic piston and a locking ring. Hydraulic pressure is supplied to the joints by an electric motor and pump and is controlled by an electric circuit, pressure sensors and valves. When hydraulic pressure is applied, the pistons are activated, locking the joints. Hydraulic pressure can also be released to unlock the joints through a user control circuit. By separating the hydraulic system from the structural arms of the apparatus, a wider variety of materials can be selected for managing hydraulic pressure and structural strength. Advantageously, this allows for a significant reduction in the device weight and the potential for device modularity, while still maintaining device functionality.

Further examples of the surgical support apparatus of this disclosure may include one or more of the following, in any suitable combination.

In examples, the surgical support apparatus of this disclosure includes a base member and a first support member rotatably coupled at a proximal end to the base member by a first joint. The first joint includes a first piston assembly. The apparatus also includes a second support member rotatably coupled to a distal end of the first support member by a second joint. The second joint includes a second piston assembly. The apparatus also includes a third joint coupled to a distal end of the second support member. The third joint includes a third piston assembly. The apparatus also includes a drive system disposed within the base member for delivering hydraulic pressure to each of the first, second and third joints. The drive system is connected by a supply conduit to each of the first, second and third piston assemblies. The supply conduit includes a first hose extending between the first joint and the second joint, and a second hose extending between the second joint and the third joint. The first, second and third piston assemblies are configured to lock and unlock the first, second and third joints, respectively, in response to the hydraulic pressure delivered by the drive system.

In further examples of the surgical support apparatus, the base member includes a mounting member for attaching the apparatus to a support structure. The mounting member is configured to allow 360 degrees of rotation between the apparatus and the support structure. In examples, the support structure is selected from one of a table, a chair or a wall of an operating room. In examples, the first joint is a double ball-and-socket joint and the first piston assembly includes a first piston sub-assembly and a second piston sub-assembly. Each of the first and second piston sub-assemblies are disposed within respective joints of the double ball-and-socket joint. In examples, the supply conduit comprises a third tube extending between the joints of the double ball-and-socket joint. The third tube is capable of swiveling. In examples, the second joint is configured as a hinge to allow 360 degrees of rotation between the first support member and the second support member. The second joint includes a fixed cylinder and a 90 degree elbow. In examples, the third joint is a single ball-and-socket joint.

In yet further examples, each of the first, second and third piston assemblies includes a piston and a locking ring. The base member further includes at least one user activation control. In examples, the at least one user activation control is selected from a group consisting of a power switch, an activation button, a remote switch, and a foot pedal. The hydraulic pressure is supplied by a pump and a motor of the drive system. The hydraulic pressure is controlled by a circuit board and at least one valve of the drive system. In examples, the at least one valve is one of a solenoid valve, a check valve, and a relief valve. The drive system further includes a reservoir for holding a fluid. An adaptor is releasably coupled to the third joint for attachment to a tool or an instrument. The hydraulic pressure locks and unlocks each of the first, second, and third joints simultaneously. In examples, the apparatus is configured for use in a sterile field. In other examples, at least a portion of the apparatus is covered with a sterile drape.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
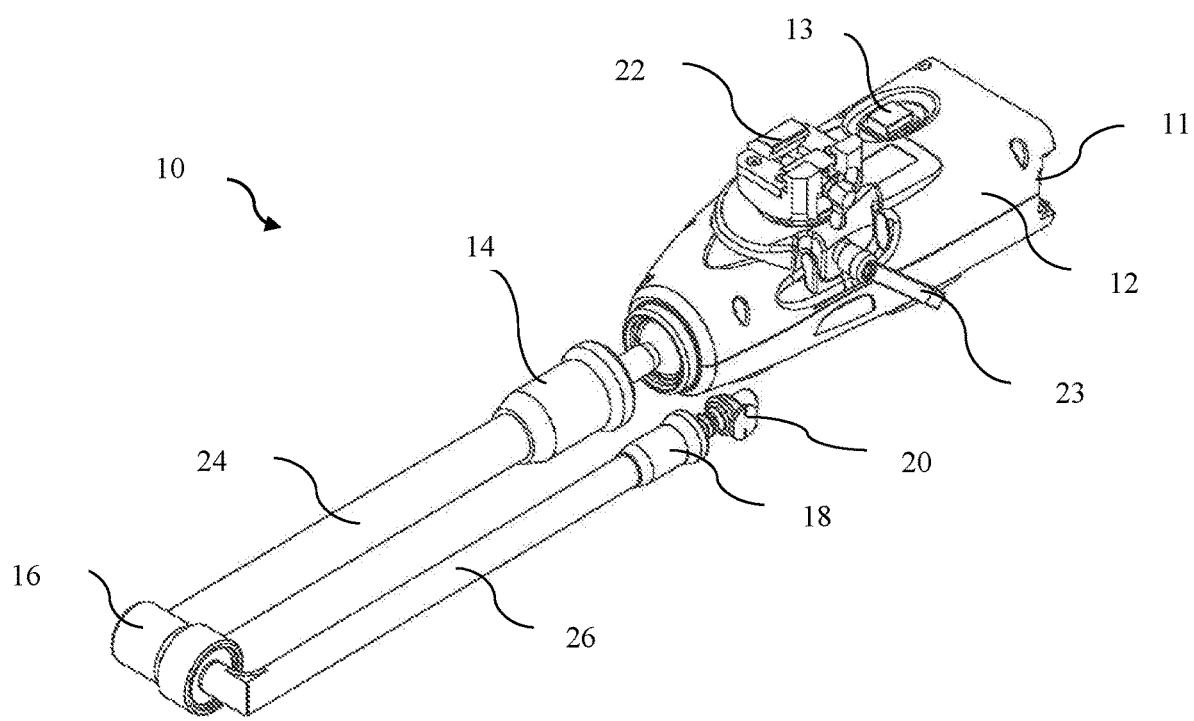
FIGS. 1A and 1B illustrate an exemplary surgical support apparatus of this disclosure in a perspective view (FIG. 1A) and a side view (FIG. 1B)

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Turning now to FIG. 1A, a perspective view of an exemplary surgical support apparatus 10 of this disclosure is shown. The apparatus 10 includes a base 12 having a mounting member 22, such as a universal rail clamp, for attaching the apparatus 10 to a support structure, such as an operating table or chair, or a wall of the operating room. The mounting member 22 may be operated by means of a user control 23. A proximal end 11 of the base 12 may include a power supply attachment (not shown) for a power supply, such as a battery. A user control 13, such as a power switch, may also be provided. The apparatus 10 further includes a base joint 14, a mid-joint 16, and a remote joint 18. The remote joint 18 is configured to provide support for items to be held in position by the apparatus 10. For example, a tool mount or instrument adapter 20 may be releasably coupled to the remote joint 18 to secure the items to be held by the distal end of the apparatus 10.

In examples, the base joint 14 is a double ball-and-socket joint, the mid-joint 16 is a hinge joint, and the remote joint 18 is a single ball-and-socket joint. However, different types of joints and joint arrangements are contemplated by this disclosure. A first rigid support member 24, which may be tubular in construction to resist deflection and torsion forces, interconnects the base joint 14 with the mid-joint 16. Extending from the mid-joint 16 is a second rigid support member 26, which may also be tubular in construction to be resistant to deflection and torsion forces. However, alternate structural components, such as custom extrusions or other geometric configurations of the support members 24, 26, are contemplated by this disclosure. Additionally, alternate numbers of support members, such as three, four or five, are contemplated by this disclosure. Notably, each additional support member would require at least one additional joint, preferably a rotational joint, to form the apparatus 10.

Figure 1B:
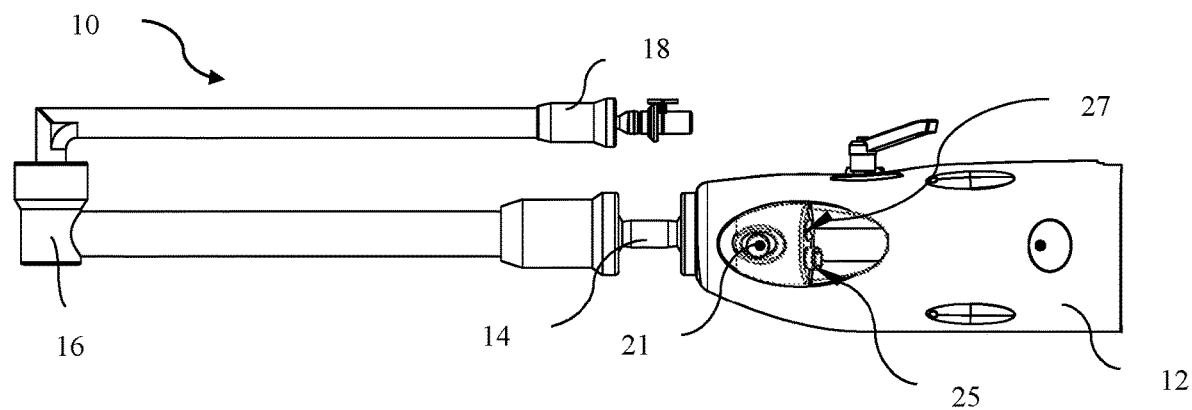

FIG. 1B is a side view of the apparatus 10 of FIG. 1A. In FIG. 1B, it can be seen that the base 12 further includes a number of user activation controls, such as an activation button 21 and a remote switch connection 25 for a remote switch (not shown). The base 12 may also include a foot pedal connection 27 for a foot pedal activation member (not shown). Other user actuators, such as voice controls, are also contemplated by this disclosure. Additionally, a manual lock and unlock backup or override mechanism for use in case of actuator failure may also be provided. A user can thus lock and unlock the joints 14, 16, 18 through one or more of the user activation controls, as further described below.

Figure 2A:
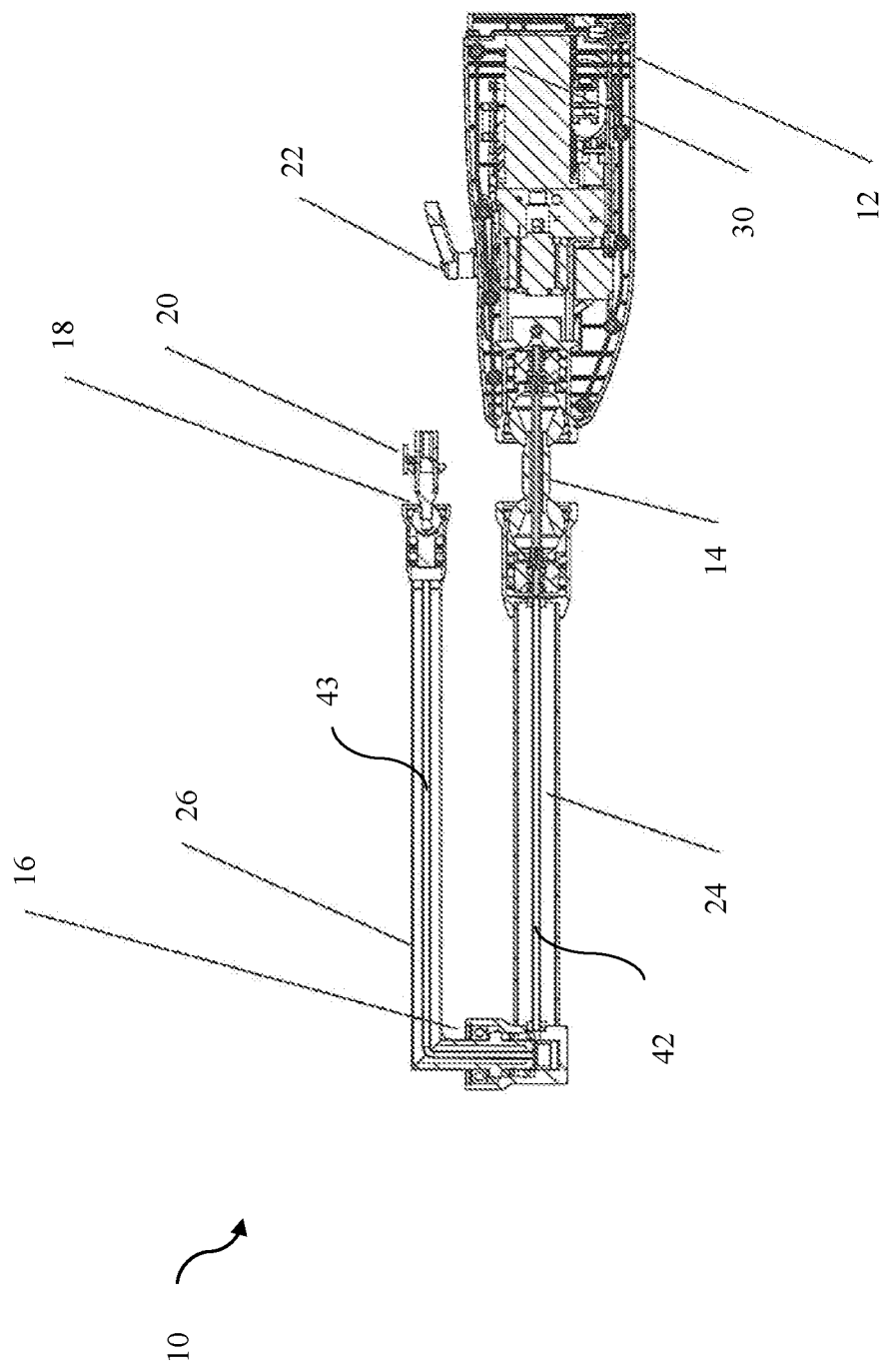
FIG. 2A is a cross-sectional view of the surgical support apparatus of FIGS. 1A and 1B.
Figure 2B:
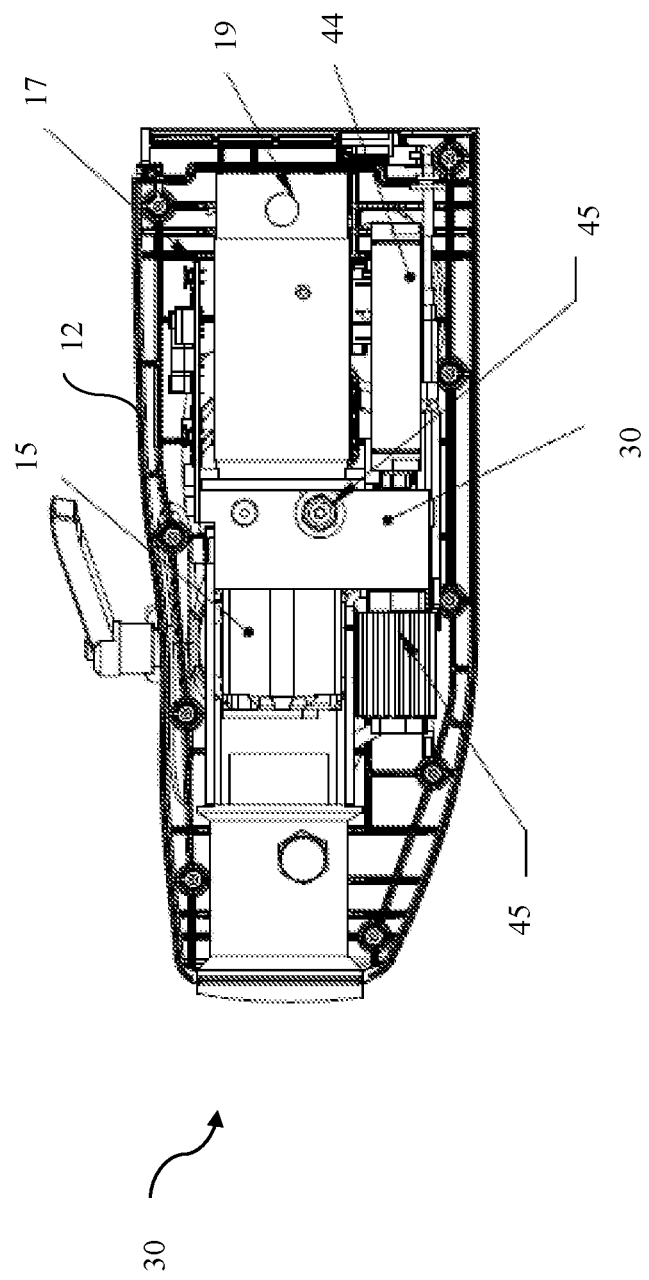
FIG. 2B is a detailed, cross-sectional view of the base of the surgical support apparatus of FIGS. 1A and 1B.

FIG. 2A shows the apparatus 10 of FIGS. 1A and 1B in a cross-sectional view. In FIG. 2A, it can be seen that a hydraulic drive system 30 is enclosed within the base 12. Connected to the drive system 30 is a continuous series of hydraulic pressure tubing that runs through each joint 14, 16, 18. Specifically, a first pressure tube 42 extends between the base joint 14 and the mid-joint 16, and a second pressure tube 43 extends between the mid-joint 16 and the remote joint 18. The drive system 30 is shown in more detail in FIG. 2B. In FIG. 2B, hydraulic pressure is supplied by a pump 15 and an electric motor 19 housed within the base 12. Hydraulic pressure is furthermore controlled by an electric circuit board 17. However, other systems for applying hydraulic pressure, such as pneumatic systems, are also contemplated by this disclosure. The drive system 30 may also include a source of pressurized fluid, such as a reservoir 44, along with one or more pressure sensors (not shown). Control valves 45, which may include at least one of a solenoid valve, a check valve, and a relief valve, control the supply of fluid from the reservoir 44 and the pressure from the motor 19 and the pump 15. The control valves 45 can be manipulated by the user, for example, by depressing a foot pedal, to reconfigure the control valves 45 to discharge the pressurized fluid in the reservoir 44 into the hydraulic pressure system.

Figure 3:
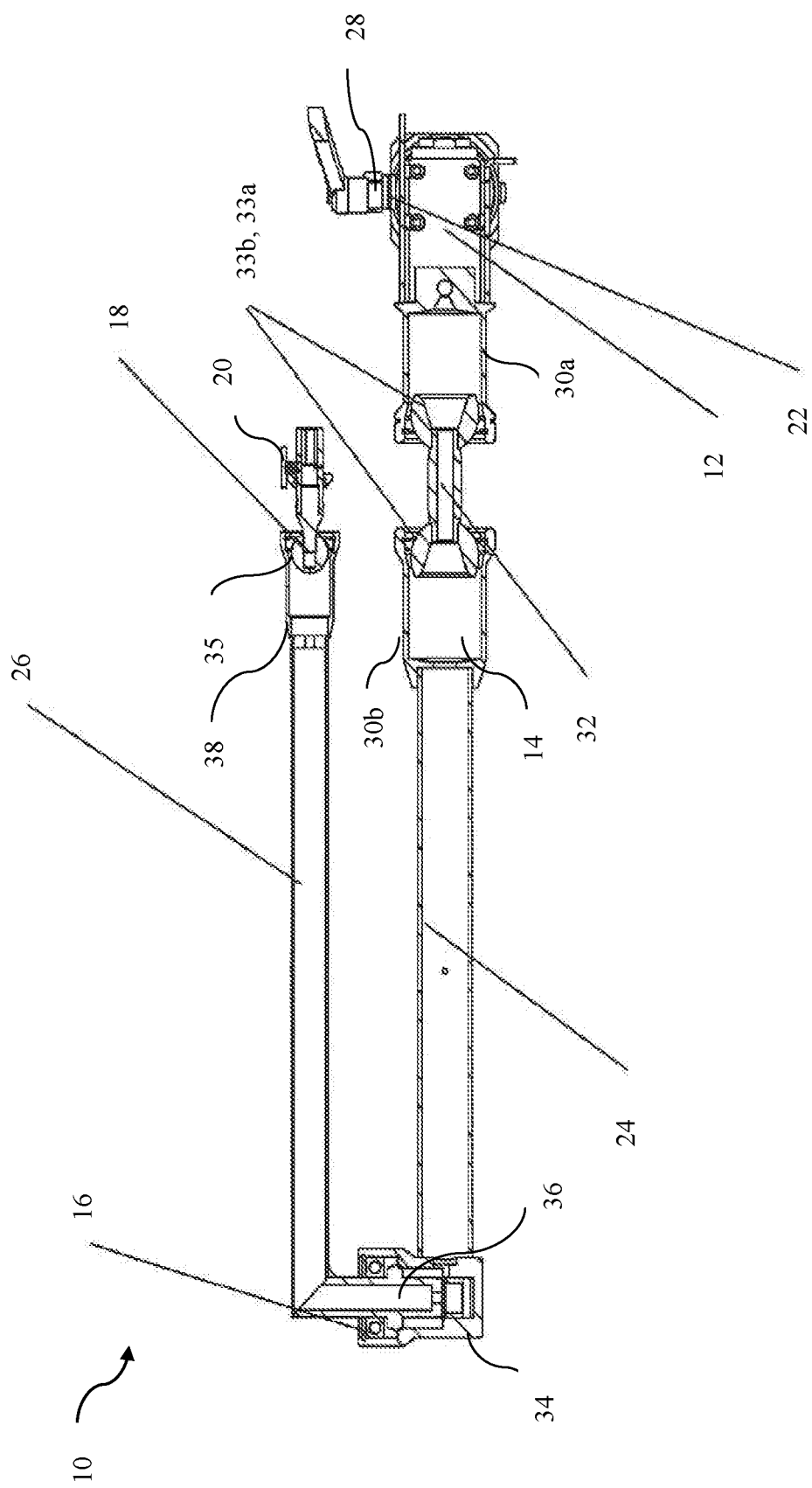
FIG. 3 is a cross-sectional view of the structural components of the surgical support apparatus with the hydraulic components removed.

Turning now to FIG. 3, the structural members of the apparatus 10 of FIGS. 1A and 1B are illustrated in more detail with the hydraulic components removed. As stated above, the mounting member 22 is used to secure the apparatus 10 to a support structure, such as an operating room table rail. The mounting member 22 includes a lockable rotational joint 28 that allows the entire apparatus 10 to rotate 360 degrees relative to the support structure. Mounted to the base 12 is the base joint 14, which consists of a first cylinder 30a and a second cylinder 30b. A first ball assembly 33a disposed within the first cylinder 30a is connected to a second ball assembly 33b disposed within the second cylinder 30b by a structural support 32 which is configured to prevent the relative movement of first ball assembly 33a with respect to second ball assembly 33b. The double ball-and-socket arrangement of the base joint 14 advantageously provides a greater range of motion to the base joint 14 than a single ball-and-socket arrangement. The mid-joint 16 consists of a fixed cylinder 34 and a 90 degree elbow 36 which connects the second support member 26 to the mid-joint 16. The mid-joint 16 is configured to allow 360 degrees of rotation between the first support member 24 and the second support member 26. The remote joint 18 comprises a remote ball assembly 35 disposed within a housing 38. In examples, the entire apparatus 10 is covered with a sterile barrier, such as a drape (not shown), to allow the apparatus 10 to be used within a sterile field. Non-limiting examples of sterile drapes are described in U.S. Publication No. 2011/0088702 to Tenet Medical Engineering, Inc., the entire contents of which are incorporated herein by reference. An optional remote switch on the drape can also be used for remote activation by the user.

Figure 4:
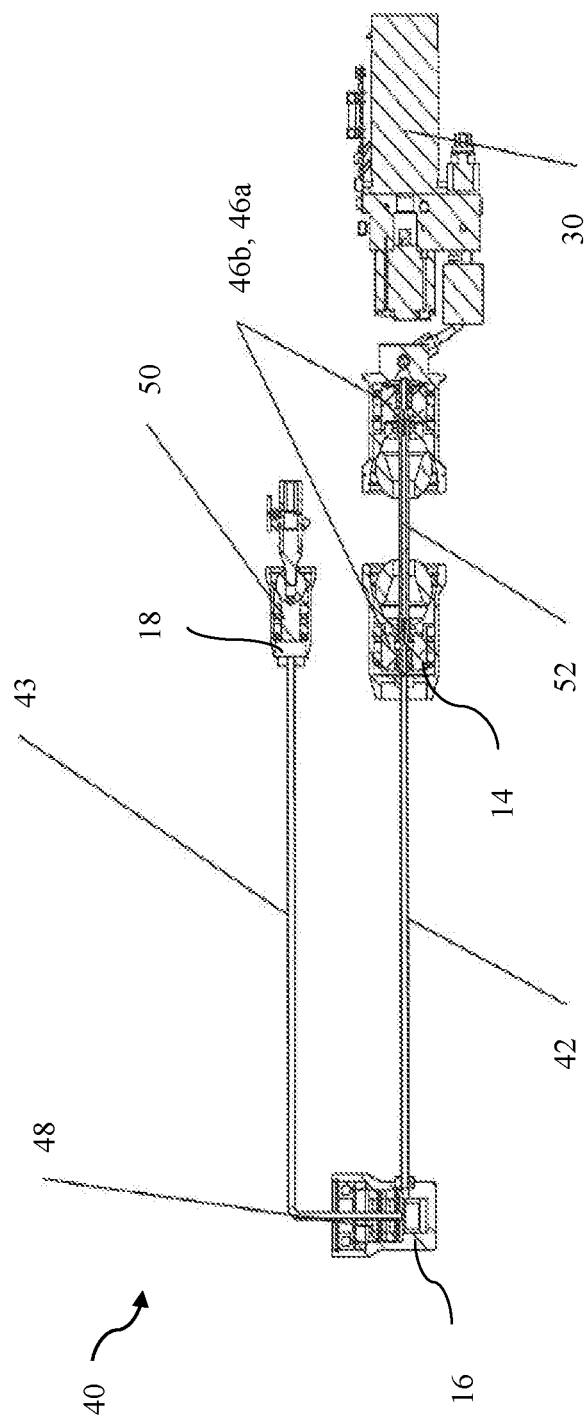
FIG. 4 is a cross-sectional view of the hydraulic system of the surgical support apparatus with the structural components removed.

FIG. 4 illustrates an exemplary hydraulic pressure system 40 of this disclosure for use with, for example, the apparatus 10 of FIG. 3. The drive system 30, together with the pressure tubes 42, 43, form the hydraulic pressure system 40. Each joint 14, 16, 18 is open to the hydraulic pressure system 40 through a sealed piston assembly. For example, the base joint 14 is open to the system 40 through the base joint piston sub-assemblies 46a, 46b. The mid-joint 16 is open to the system 40 through the mid-joint piston assembly 48, and the remote joint 18 is open to the system 40 through the remote joint piston assembly 50. The base joint piston sub-assemblies 46a, 46b are connected by a swivel pressure hose 52. In examples, when pressured, the piston assemblies 46a, 46b, 48 and 50 engage the structural members of the joints 14, 16, 18 and simultaneously apply locking forces, as described in more detail below. However, independent locking and unlocking of each joint 14, 16, 18 individually is also contemplated by this disclosure. For example, additional pressure tubes could extend between the joints 14, 16, 18 to isolate the hydraulic pressure at each joint.

Figure 5A:
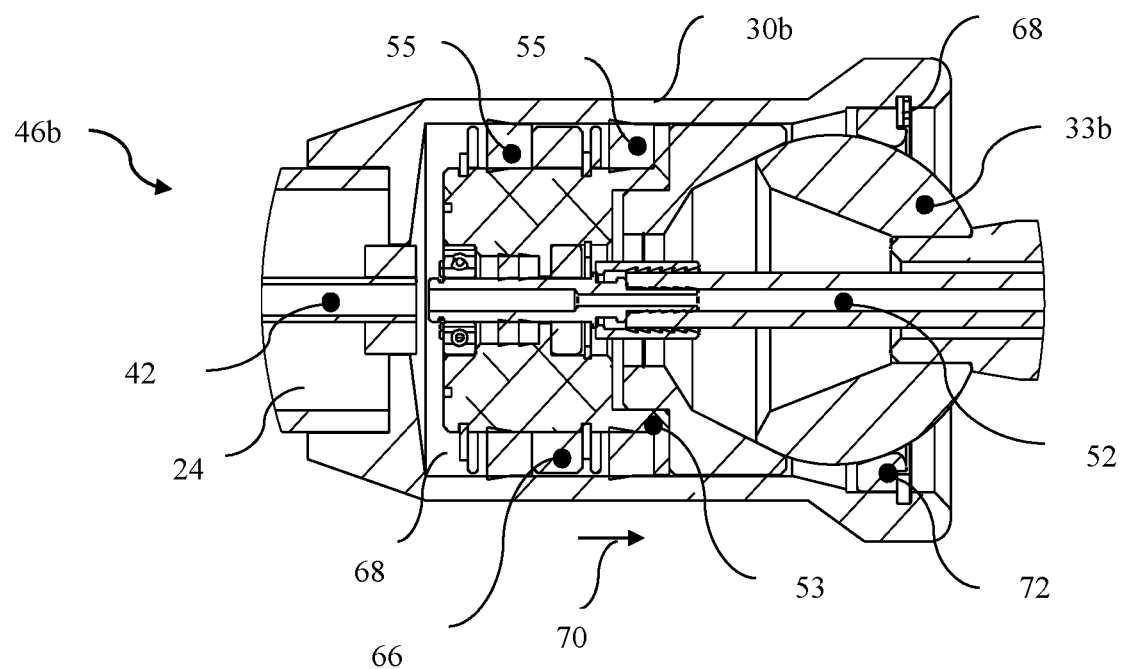
FIGS. 5A-C are cross sectional views of the individual joints of the surgical support apparatus of FIGS. 1A and 1B.

The discussion will now turn to FIG. 5A, which shows an enlarged view of the base joint piston sub-assembly 46b (base joint piston sub-assembly 46a being substantially a mirror image thereof). As shown in FIG. 5A, a piston 53 is axially, slideably displaceable within the second cylinder 30b. In examples, one or more seals 55 circumscribe the piston 53 to establish a seal between the piston 53 and the second cylinder 30b. The seals 55 are separated by one or more spacers 66. The seals 55 and the spacers 66 are retained in place by a retaining ring 68. The pressure hose 52 attached to subassembly 46a (FIG. 4) allows pressurized fluid from the sub-assembly 46a to communicate with the sub-assembly 46b. The pressure hose 52 is also sealingly coupled within the second cylinder 30b by the seals 55. Because of the pressure hose 52, pressurized fluid is supplied to the sub-assemblies 46a, 46b simultaneously.

To lock the second ball assembly 33b with respect to the second cylinder 30b (and, similarly, the first ball assembly 33a with respect to the first cylinder 30a), the pressurized fluid is supplied to an area of the sub-assembly 46b. The pressurized fluid applies a force to the piston 53 to urge the piston 53 in the direction of arrow 70. Consequently, the piston 53 is urged to travel in the direction of arrow 70 until it engages the second ball assembly 33b, thereby compressing the second ball assembly 33b against a locking ring 72. The second ball assembly 33b engages the locking ring 72 by, for example, a friction fit or a wedge fit. When this occurs, the second ball assembly 33b is maintained in a locked configuration with respect to the second cylinder 30b, thereby preventing any relative movement therebetween. Thus, the supply of pressurized fluid causes the base joint 14 to become locked into position. The pressurized fluid is also communicated to the first pressure tube 42 in the first support member 24 to permit the pressurized fluid to be transmitted to the mid-joint 16 (FIG. 5B).

Figure 5B:
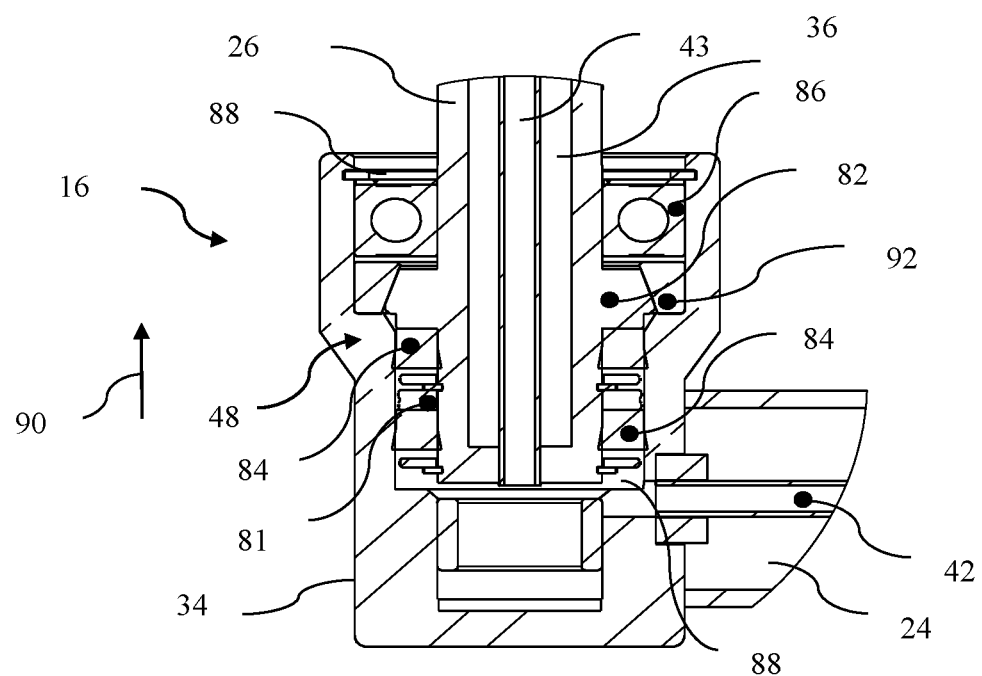

Mid-joint 16 is shown in an enlarged view in FIG. 5B. In FIG. 5B, a piston 82 is axially, slideably displaceable within the fixed cylinder 34. The piston 82 is separated from a retaining ring 88 by bearings 86. In examples, one or more seals 84 circumscribe the piston 82 to establish a seal between the piston 82 and the fixed cylinder 34. The seals 84 are separated by one or more spacers 81. The seals 84 and the spacers 81 are retained in place by the retaining ring 88. To lock the mid-joint piston assembly 48 with respect to the fixed cylinder 34, the pressurized fluid is supplied to an area of the mid-joint piston assembly 48. The pressurized fluid applies a force to the piston 82 to urge the piston 82 in the direction of arrow 90. Consequently, the piston 82 is urged to travel in the direction of arrow 90 until the piston 82 engages the locking ring 92. The piston 82 engages the locking ring 92 by, for example, a friction fit or a wedge fit. When this occurs, the elbow 36 is maintained in a locked configuration with respect to the housing 34, thereby preventing any relative movement therebetween. Thus, the supply of pressurized fluid causes the mid-joint 16 to become locked in position. The pressurized fluid is also communicated to the second pressure tube 43 in the second support member 26 to permit the pressurized fluid to be transmitted to the remote joint 18 (FIG. 5C).

Figure 5C:
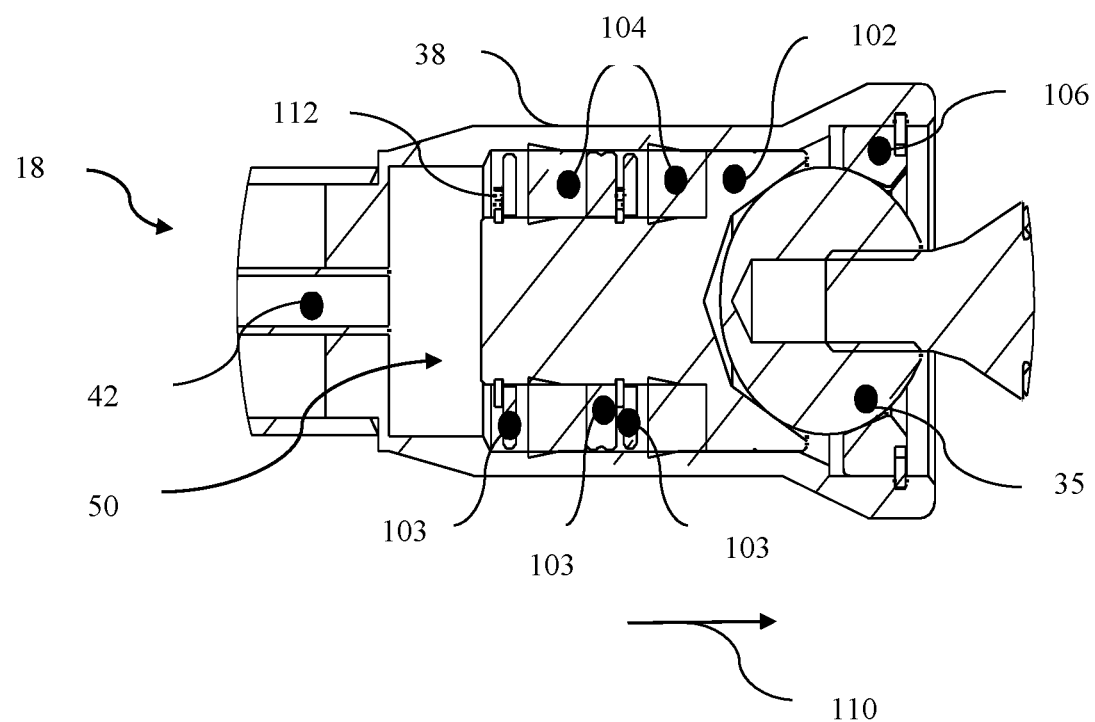

FIG. 5C is an enlarged view of the remote joint 18, including the remote joint piston assembly 50 disposed within the housing 38. A piston 102 is axially, slideably displaceable within the housing 38. In examples, one or more seals 104 circumscribe the piston 102 to establish a seal between the piston 102 and the housing 38. The seals 104 are separated by one or more spacers 103. To lock the remote joint 18, the pressurized fluid is supplied to an area of the remote joint piston assembly 50. The pressurized fluid applies a force to the piston 102 to urge the piston 102 in the direction of arrow 110. Consequently, the piston 102 is urged to travel in the direction of arrow 110 until the remote ball assembly 35 engages a locking ring 106, thereby compressing the remote ball assembly 35 against the locking ring 106. The remote ball assembly 35 engages the locking ring 106 by, for example, a friction fit or a wedge fit. When this occurs, the remote ball assembly 35 is maintained in a locked configuration with respect to the housing 38, thereby preventing any relative movement therebetween. Thus, the supply of pressurized fluid causes the remote joint 18 to become locked in position.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:
1. A surgical support apparatus comprising:
 a base member comprising a housing;
 a first support member rotatably coupled at a proximal end to the housing of the base member by a first joint, the first joint comprising a first piston assembly;

a second support member rotatably coupled to a distal end of the first support member by a second joint, the second joint comprising a second piston assembly;

a third joint coupled to a distal end of the second support member, the third joint comprising a third piston assembly; and a drive system disposed within the housing of the base member for delivering hydraulic pressure to each of the first, second and third joints, the drive system connected by a supply conduit to each of the first, second and third piston assemblies, the drive system comprising a reservoir separate from the supply conduit and configured to deliver a fluid to the supply conduit;

wherein each of the first, second and third piston assemblies comprises a piston and a locking ring for locking the respective first, second and third joints into position;

wherein the supply conduit comprises a first tube extending between the first joint and the second joint, and a second tube extending between the second joint and the third joint;

wherein the first, second and third piston assemblies are configured to lock and unlock each of the first, second and third joints, respectively, in response to the hydraulic pressure delivered by the drive system; and wherein the hydraulic pressure locks and unlocks each of the first, second, and third joints simultaneously.

2. The apparatus of claim 1, further comprising a mounting member on an outer surface of the housing of the base member for attaching the apparatus to a support structure.

3. The apparatus of claim 2, wherein the mounting member is configured to allow 360 degrees of rotation between the apparatus and the support structure.

4. The apparatus of claim 2, wherein the support structure is selected from one of a table, a chair or a wall of an operating room.

5. The apparatus of claim 1, wherein the first joint is a double ball-and-socket joint and the first piston assembly comprises a first piston sub-assembly and a second piston sub-assembly, each of the first and second piston sub-assemblies being disposed within respective joints of the double ball-and-socket joint.

6. The apparatus of claim 5, wherein the supply conduit comprises a third tube extending between the joints of the double ball-and-socket joint, the third tube being capable of swiveling.

7. The apparatus of claim 1, wherein the second joint is configured as a hinge to allow 360 degrees of rotation between the first support member and the second support member.

8. The apparatus of claim 1, wherein the second joint comprises a fixed cylinder and a 90 degree elbow.

9. The apparatus of claim 1, wherein the third joint is a single ball-and-socket joint.

10. The apparatus of claim 1, wherein each of the first, second and third piston assemblies are housed within a housing of a respective one of the first, second and third joints.

11. The apparatus of claim 1, wherein the base member further comprises at least one user activation control.

12. The apparatus of claim 11, wherein the at least one user activation control is selected from a group consisting of a power switch, an activation button, a remote switch, and a foot pedal.

13. The apparatus of claim 1, wherein the hydraulic pressure is supplied by a pump and a motor of the drive system.

14. The apparatus of claim 1, wherein the hydraulic pressure is controlled by a circuit board and at least one valve of the drive system.

15. The apparatus of claim 14, wherein the at least one valve is one of a solenoid valve, a check valve, and a relief valve.

16. The apparatus of claim 1, further comprising an adaptor releasably coupled to the third joint to a tool or an instrument.

17. The apparatus of claim 1, wherein the apparatus is configured for use in a sterile field.

18. The apparatus of claim 1, wherein at least a portion of the apparatus is covered with a sterile drape.

* * * * *